(12) United States Patent
Davis

(10) Patent No.: US 7,767,857 B1
(45) Date of Patent: Aug. 3, 2010

(54) PREPARATION OF 2,4,6,-TRICHLOROANILINE FROM ANILINE USING N-CHLORO REAGENTS

(75) Inventor: Matthew C. Davis, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 12/415,776

(22) Filed: Mar. 31, 2009

(51) Int. Cl.
*C07C 209/74* (2006.01)
(52) U.S. Cl. ...................................... 564/412
(58) Field of Classification Search ........................ None
See application file for complete search history.

(56) References Cited

OTHER PUBLICATIONS

Database CAPLUS on STN, Acc. No. 2003:126035, Muathen, Helvetica Chimica Acta (2003), 86(1), p. 164-168 (abstract).*
Database CAPLUS on STN, Acc. No. 1929:42789, Erdelyl, Magyar Chemiai Folyoirat (1929), 35, p. 15-16 (abstract).*

* cited by examiner

*Primary Examiner*—Brian J Davis
(74) *Attorney, Agent, or Firm*—Charlene A. Haley

(57) ABSTRACT

A product-by-process and method of manufacturing 2,4,6-trichloroanailine intermediates. The method of manufacturing 2,4,6-trichloroanailine intermediates by utilizing solvents and N-chlorinating reagents.

14 Claims, No Drawings

PREPARATION OF 2,4,6,-TRICHLOROANILINE FROM ANILINE USING N-CHLORO REAGENTS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to methods of manufacturing 2,4,6-trichloroaniline intermediates, more specifically, utilizing solvents and N-chlorinating reagents in the method of manufacturing 2,4,6-trichloroanailine intermediates.

BACKGROUND OF THE INVENTION

In military applications, 2,4,6-trichloroaniline (TCA) is utilized for the preparation of insensitive energetic material (TATB) that is employed in several Navy weapons systems. Currently, TCA is not manufactured domestically; most likely due to the hazards of using chlorine gas. The synthesis of 2,4,6-trichloroaniline has almost invariably been accomplished by chlorination of aniline with chlorine or sulfuryl chloride. (Muathen, H. A. Helv. Chim. Acta. 2003, 86, 164-168; Hofmann, A. W. Ann. 1845, 53, 1-57; Meyer, V.; Sudborough, J. J. Ber. 1894, 27, 3146-3153; Sudborough, J. J. J. Chem. Soc. 1894, 65, 1028-1031; Chattaway, F. D.; Irving, H. J. Chem. Soc. 1933, 142-143; Orloff, H. D.; Napolitano, J. P. U.S. Pat. No. 2,675,409, Apr. 13, 1954; Werner, F.; Roxo, B.; Mannes, K.; Trescher, V. U.S. Pat. No. 4,447,647, May 8, 1984; Kim, C.-U.; Jin, H.-J.; Lee, S.-B.; Lee, J.-M. Hwahak Konghak. 1990, 28, 230-236. Q4; Mehilal.; Salunke, R. B.; Agrawal, J. P. Indian J. Chem., Sect. B. 2002, 41, 604-607; Wenghoffer, L. J. Prakt. Chem. 1877, 16, 448-466; Eller, W.; Klemm, L. Ber. 1922, 55, 217-224.) Although the latter reactions typically provide TCA in high yield, these reagents require special handling because of their highly corrosive nature. In addition, chlorine and, especially, sulfur dioxide emissions must be strictly controlled. (U.S. Clean Air Act. Public Law 101-549, 1990.)

The synthesis of TCA by means other than chlorine gas are few (Muathen, H. A. Helv. Chim. Acta. 2003, 86, 164-168). Chlorine gas is highly toxic and difficult to work with owing to its highly corrosive nature. Domestic manufacture of has ceased probably on account of these problems. There exists a need in the art for procedures that are safer and use less toxic N-chloro reagents to make TCA.

More convenient reagents for aromatic chlorinations are N-chloro reagents including, but not limited to, N-chlorosuccinimide (NCS). The chlorination of aniline and substituted anilines with N-chloro reagents, including NCS, has been studied. (Chao, T. H.; Cipriani, L. P. J. Org. Chem. 1961, 26, 1079-1081; Searle, N. E.; Cupery, H. E. J. Org. Chem. 1954, 19, 1622-1627; Neale, R. S.; Schepers, R. G.; Walsh, M. R. J. Org. Chem. 1964, 29, 3390-3393.) The main concern of these studies was determining the ortho-para regioselectivity of monochlorination. Other literature reports showed that 4-bromoaniline and 3,5-difluoro-4-iodoaniline undergo dichlorination at the 2,6-position in chloroform with NCS or N-chloro-2,4-dichloroacetanilide. (Reed, W. W.; Orton, K. J. P. J. Chem. Soc. 1907, 91, 1543-1554; Manka, J. T.; Kaszynski, P. J. Flourine Chem. 2003, 124, 39-43.) Previously, there was no reported instance of the study of tri-chlorination of an aniline using N-chloro reagents.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention generally relate to methods of manufacturing 2,4,6-trichloroanailine intermediates which utilize solvents and N-chlorinating reagents.

The invention relates to the use of N-chloro reagents to effect regioselective trichlorination of aniline at the 2,4,6-positions exclusively. The N-chloro reagents useful in the process include, but are not limited to, N-chlorosuccinimide, N-chloro-2,4-dichloroacetaniline, trichloroisocyanuric acid, N-chlorodialkylamines, 1,3-dichloro-5,5-dimethylhydantoin, chloramines T, monosodium salt dichloroisocyanuric acid, hexachloromelamine, N-chlorotriethylammonium chlroride, N-chloropiperidine, and N-chloromorpholine.

Solvents useful for the process include, but not limited to, Polar aprotic: acetonitrile, propionitrile, chloroform, dimethylformamide, methylisobutylketone, dimethoxyethane, tetrahydrofuran, acetone, N-methylpyrrolidone, dimethylsulfoxide, and pyridine. Polar protic compounds include, but not limited to, water, methanol, ethanol, isopropanol, t-butanol, 1,2-propanediol, acetic acid. Nonpolar compounds include, but not limited to, toluene, heptanes, methyl t-butylether, and carbon tetrachloride. Halogenated compounds include, but not limited to, methylene chloride, chloroform, 1,2 dichloroethane, carbon tetrachloride, and chlorobenzene.

An example of the process is shown in Scheme 1, where conditions (a) are three equivalents NCS and acetonitrile solvent at reflux temperature.

Scheme 1.

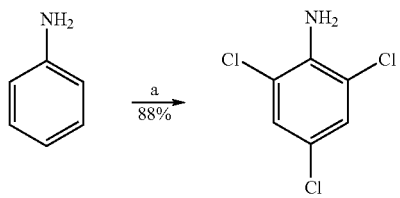

The following working example is for illustration purposes only and not to be used to limit any of the embodiments.

Chlorination of Aniline 2,4,6-Trichloroaniline (TCA)

A 5-L, two-necked, round-bottomed flask equipped with magnetic stirbar was charged with 50 g freshly distilled aniline (0.54 mol) in 1 L MeCN. One neck was equipped with a reflux condenser and $N_2$ purge, and the second neck was glass stoppered. The solution was brought to reflux. N-Chlorosuccinimide (86 g, 1 equiv) was added through the glass-stoppered neck in one portion. The color of the reaction became purple-brown. After 1 h, a second addition of 86 g NCS (1 equiv) was made in one portion. After 1 h, NMR of the reaction mixture showed only traces of NCS remained in addition to formation of primarily 2,4-dichloroaniline. The final addition of 86 g NCS (1 equiv) was made in eight ~10-g portions, reaction occurs with a vigorous exotherm. After the addition, TLC showed the reaction was complete. The mixture was cooled to room temperature and poured into 3 L vigorously stirred $H_2O$. After stirring 1 h, the light purple solid was collected on a coarse-porosity glass frit, washed with 1 L $H_2O$, and air-dried on the frit for 2 h. The crude was dissolved in 1 L $Et_2O$ and washed with 500 mL $H_2O$ and 500 mL brine. The organic layer was dried with anhydrous $MgSO_4$ and filtered. The filtrate was treated with 11 g Darco G-60 for 1 h. The mixture was filtered through diatomaceous earth, and the solvent was rotary evaporated. The red-brown solid was dissolved in 1 L hexanes. The solution was filtered through 300 g $SiO_2$ on a medium-porosity glass frit that removed most of the color. The filtrates were rotary evaporated, leaving 111.6 g of the title compound as a pale yellow solid that was >97% by 1 H NMR (88%). Recrystallization from EtOH gave the title compound in analytically pure form as soft, colorless needles. Mp 68-70° C., 77.5° C. $\delta_H$(CDCl$_3$): 7.13 (s, 2 H), 4.36 (bs, $NH_2$); $\delta_C$ (CDCl$_3$): 139.24, 127.81, 122.06, 119.92. Elemental analysis calculated for $C_6H_4Cl_3N$: C, 36.68; H, 2.05; N, 7.13. Found: C, 36.87; H, 1.93; N, 7.07.

Embodiments of the invention demonstrate that aniline can be trichlorinated at the 2,4,6-positions in excellent yield by the reaction of aniline with three equivalents of an N-chloro reagent in a solvent. One equivalent of N-chloro reagents causes mono-chlorination at the 2- or 4-position. The next equivalent of N-chloro reagent causes chlorination at the unreacted 2- or 4-position. And the final equivalent of N-chloro reagent, causes chlorination at the 6-position.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method of making 2,4,6,-trichloroaniline intermediate (B), comprising:

preparing a mixture of aniline (A) with a solvent until solution is brought to reflux, wherein said solvent is selected from the group consisting of polar aprotic solvents, halogenated solvents, protic solvents, and hydrocarbon solvents;

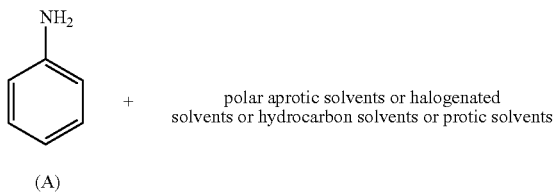

(A)

adding intervals of an N-Chlorinating reagent until reaction has completed and the resultant mixture is substantially 2,4,6-trichloroaniline;
cooling said resultant mixture to about room temperature;
adding said mixture to $H_2O$ and stirring said mixture until a first crude was formed;
dissolving first said crude in a solvent and washing said mixture with $H_2O$ and brine;
drying said mixture with an anhydrous salt and filtering said crude and evaporating solvent and a second solid was formed; and
dissolving said second solid in a hexane solution and filtering and evaporating said solution to form a third solid being 2,4,6-trichloroaniline intermediate (B)

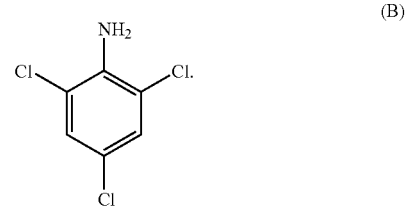

2. The method of claim 1, wherein said solvent is said polar aprotic compound selected from the group consisting of acetonitrile, propionitrile, chloroform, dimethylformamide, methylisobutylketone, dimethoxyethane, tetrahydrofuran, acetone, N-methylpyrrolidone, dimethylsulfoxide, and pyridine.

3. The method of claim 1, wherein said solvent is said halogenated compound selected from the group consisting of methylene chloride, chloroform, 1,2 dichloroethane, carbon tetrachloride, and chlorobenzene.

4. The method of claim 1, wherein said solvent is said polar protic compound selected from the group consisting of acetic acid, water, methanol, ethanol, isopropanol, t-butanol, and 1,2-propanediol.

5. The method of claim 1, wherein said solvent is said hydrocarbon compound selected from the group consisting of toulene, heptanes, methyl t-butylether, and carbon tetrachloride.

6. The method of claim 1, wherein said N-Chlorinating agent is N-Chlorosuccimide.

7. The method of claim 1, wherein said N-Chlorinating agent is selected from the group consisting of N-chloro-2,4-dichloroacetaniline, trichloroisocyanuric acid, N-chlorodialkylamines, 1,3-dichloro-5,5-dimethylhydantoin, chloramines T, monosodium salt dichloroisocyanuric acid, hexachloromelamine, N-chlorotriethylammonium chlroride, N-chloropiperidine, and N-chloromorpholine.

8. A method of manufacturing a 2,4,6-trichloroaniline intermediate, comprising:

preparing a mixture of aniline (A) with a solvent until solution is brought to reflux; wherein said solvent is selected from the group consisting of polar aprotic solvents, halogenated solvents, hydrocarbon solvents

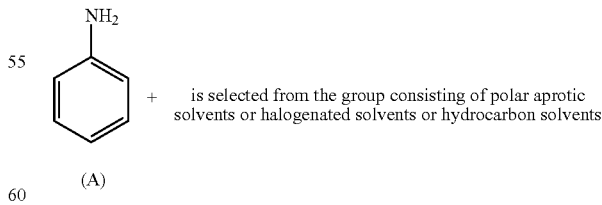

(A)

adding intervals of N-Chlorinating agent until reaction has completed and the resultant mixture is substantially 2,4,6-trichloroaniline;
cooling said resultant mixture to about room temperature;
adding said mixture to $H_2O$ and stirring said mixture until a first crude was formed;

dissolving first said crude in Et$_2$O and washing said mixture with H$_2$O and brine;
drying said mixture with an anhydrous salt and filtering said crude and evaporating solvent and a second solid was formed; and
dissolving said second solid in a hexane solution and filtering and evaporating said solution to form a third solid being 2,4,6-trichloroaniline intermediate (D)

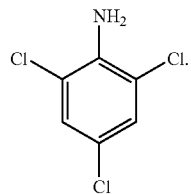
(D)

9. The method of claim 8, wherein said solvent is a polar aprotic compound selected from the group consisting of acetonitrile, propionitrile, chloroform, dimethylformamide, methylisobutylketone, dimethoxyethane, tetrahydrofuran, acetone, N-methylpyrrolidone, dimethylsulfoxide, and pyridine.

10. The method of claim 8, wherein said solvent is a halogenated compound selected from the group consisting of methylene chloride, methylene chloride, chloroform, 1,2 dichloroethane, carbon tetrachloride, and chlorobenzene.

11. The method of claim 8, wherein said solvent is a polar protic compound selected from the group consisting of acetic acid, water, methanol, ethanol, isopropanol, t-butanol, and 1,2-propanediol.

12. The method of claim 8, wherein said solvent is a hydrocarbon compound selected from the group consisting of toulene, heptanes, and methyl t-butylether.

13. The method of claim 8, wherein said N-Chlorinating agent is N-Chlorosuccimide.

14. The method of claim 8, wherein said N-Chlorinating agent is selected from the group consisting of N-chloro-2,4-dichloroacetaniline, trichloroisocyanuric acid, N-chlorodialkylamines, 1,3-dichloro-5,5-dimethylhydantoin, chloramines T, monosodium salt dichloroisocyanuric acid, hexachloromelamine, N-chlorotriethylammonium chlroride, N-chloropiperidine, and N-chloromorpholine.

* * * * *